United States Patent
Karabchevsky

(10) Patent No.: US 11,525,785 B2
(45) Date of Patent: Dec. 13, 2022

(54) METHOD AND DEVICE FOR CHEMILUMINESCENCE-BASED ANALYSIS

(71) Applicant: B.G. NEGEV TECHNOLOGIES AND APPLICATIONS LTD., AT BEN-GURION UNIVERSITY, Beer-Sheva (IL)

(72) Inventor: Alina Karabchevsky, Haifa (IL)

(73) Assignee: B.G. NEGEV TECHNOLOGIES AND APPLICATIONS LTD., AT BEN-GURION UNIVERSITY, Haifa (IL)

(*) Notice: Subject to any disclaimer, the term of this patent is extended or adjusted under 35 U.S.C. 154(b) by 58 days.

(21) Appl. No.: 16/312,821

(22) PCT Filed: Jun. 25, 2017

(86) PCT No.: PCT/IL2017/050701
§ 371 (c)(1),
(2) Date: Dec. 21, 2018

(87) PCT Pub. No.: WO2017/221258
PCT Pub. Date: Dec. 28, 2017

(65) Prior Publication Data
US 2019/0195806 A1    Jun. 27, 2019

Related U.S. Application Data

(60) Provisional application No. 62/353,578, filed on Jun. 23, 2016.

(51) Int. Cl.
*G01N 21/76* (2006.01)
*G01N 21/05* (2006.01)
(Continued)

(52) U.S. Cl.
CPC .......... *G01N 21/76* (2013.01); *B01L 3/5027* (2013.01); *G01N 21/05* (2013.01); *G01N 33/582* (2013.01);
(Continued)

(58) Field of Classification Search
CPC .... G01N 21/76; G01N 33/582; G01N 33/587; G01N 21/05; G01N 33/725;
(Continued)

(56) References Cited

U.S. PATENT DOCUMENTS

2013/0052653 A1* 2/2013 Stein ............... G01N 33/54346
435/7.1
2016/0123858 A1* 5/2016 Kapur ............... G01N 15/0255
435/30

FOREIGN PATENT DOCUMENTS

WO  WO 2004/057312   7/2004
WO  WO 2014/163271   10/2014

OTHER PUBLICATIONS

Mosayyebi, et al. "Microfluidic system for chemiluminescence characterisation." May 2013. University of Southampton. pp. 1-49. (Year: 2013).*

(Continued)

*Primary Examiner* — Jennifer Wecker
*Assistant Examiner* — Michael Paul Shimek
(74) *Attorney, Agent, or Firm* — Knobbe, Martens, Olson & Bear, LLP

(57) ABSTRACT

A method for detecting an analyte reactive towards luminol, comprising the steps of: feeding into a reaction chamber an alkaline solution of luminol, noble metal nanoparticles and at least one analyte reactive towards luminol, wherein the reaction chamber is in the form of a curved channel; detecting the light emitted due to a chemiluminescence reaction taking place in said channel; and discharging a
(Continued)

reaction mass from said channel, characterized in that the average diameter of the metal nanoparticles is greater than 25 nm. Also provided is a microfluidic device for carrying out the method.

9 Claims, 3 Drawing Sheets

(51) Int. Cl.
    *G01N 33/72*     (2006.01)
    *B01L 3/00*     (2006.01)
    *G01N 33/58*     (2006.01)
    *G01N 21/03*     (2006.01)

(52) U.S. Cl.
    CPC ......... *G01N 33/587* (2013.01); *G01N 33/725* (2013.01); *B01L 2300/0663* (2013.01); *B01L 2300/0877* (2013.01); *B01L 2300/0883* (2013.01); *B01L 2300/123* (2013.01); *G01N 2021/0346* (2013.01)

(58) Field of Classification Search
    CPC ........... G01N 2021/0346; B01L 3/5027; B01L 2300/0663; B01L 2300/0877; B01L 2300/0883; B01L 2300/123
    See application file for complete search history.

(56) References Cited

OTHER PUBLICATIONS

"Smoothly". Updated May 6, 2021. Merriam-Webster.com Dictionary. Merriam-Webster. [retrieved on Jun. 15, 2021]. Retrieved from the Internet: <https://www.merriam-webster.com/dictionary/smoothly>. (Year: 2021).*

International Search Report and Written Opinion received in PCT Application No. PCT/IL2017/050701, dated Oct. 17, 2017.

Duan, C. et al: "Size-dependent inhibition and Enhancement by Gold Nanoparticles of Luminol-Ferricyanide chemiluminescence", 2007, J. Phys. Chem. C., vol. 111, pp. 4561-4566.

Haghighi, B. et al: "Flow injection chemiluminescence determination of isoniazid using luminol and silver nanoparticles", 2010, Microchemical Journal, vol. 95, pp. 192-197.

Kamruzzaman et al., "Chemiluminescence Microfluidic System of Gold Nanoparticles Enhanced LuminolSilver Nitrate for the Determination of Vitamin 612", 2013. Biomed Microdevices 15, pp. 195-202.

Karabchevsky, A. et al; "Tuning the chemiluminescence of a luminol flow using plasmonic nanoparticles", 2016, Light:Science & Applications; vol. 5; e16164, pp. 1-7—accepted article preview.

Li, S. et al: "Enhanced chemiluminescence of of the luminol—AgNO3 system by Ag nanoparticles", 2012, Luminescence, vol. 27, pp. 211-216.

Mosayyebi, Ali et al., Nanoparticle-Enhanced Chemiluminescence in Micro-Flow Injection Analysis, Optoelectronics Research Centre, University of Southhampton, Abstract of Conference Paper, Oct. 2013.

McDonald et al., "Fabrication of microfluidic systems in poly(dimethylsiloxane)", 2000. (Electrophoresis 21, pp. 27-40.

Zhang, Z-F., et al: "Gold nanoparticle-catalyzed luminol Chemiluminescence and Its Analytical applications", 2005, Anal. Chem, vol. 77, pp. 3324-3329.

Zielinska et al., "Preparation of silver nanoparticles with controlled particle size", 2009. Procedia Chemistry, pp. 1560-1566.

Karabchevsky et al., "Tuning the chemiluminescence of a luminol flow using plasmonic nanoparticles", Light: Science & Applications, pp. 1-7, Nov. 4, 2016.

Ghobadi et al., "A Review of Heat Transfer and Pressure Drop Correlations for Laminar Flow Curved Circular Ducts", Heat Transfer Engineering, 37(10):815-839 (2016).

"Spiral", Merriam-Webster, (https://www.merriam-webster.com/dictionary/spiral) Accessed Jun. 16, 2022.

"Serpentine", Merriam-Webster, (https://www.merriam-webster.com/dictionary/serpentine) Accessed Jun. 16, 2022.

"Serpentine vs. Spiral—What's the difference?" WikiDiff, (https://wikidiff.com/spiral/serpentine) Accessed Jun. 16, 2022.

* cited by examiner

METHOD AND DEVICE FOR CHEMILUMINESCENCE-BASED ANALYSIS

CROSS REFERENCE TO RELATED APPLICATIONS

This application is the U.S. National Phase under 35 U.S.C. § 371 of International Application No. PCT/IL2017/050701 filed Jun. 25, 2017, designating the U.S. and published as WO 2017/221258 A1 on Dec. 28, 2017, which claims the benefit of U.S. Provisional Application No. 62/353,578 filed Jun. 23, 2016. Any and all applications for which a foreign or domestic priority claim is identified above and/or in the Application Data Sheet as filed with the present application are hereby incorporated by reference under 37 CFR 1.57.

Certain chemical reactions yield products in excited electronic states. Decay of these excited states may produce emission of light—a process called chemiluminescence. Detection methods based on chemiluminescence are used in a wide range of applications, from forensic science to industrial biochemistry.

Perhaps the most known chemiluminescence agent is the compound luminol (5-amino-2,3-dihydro-1,4-phthalazinedione), which emits blue glow upon reacting with oxidizing species in an alkaline environment, as shown by the reaction scheme depicted below:

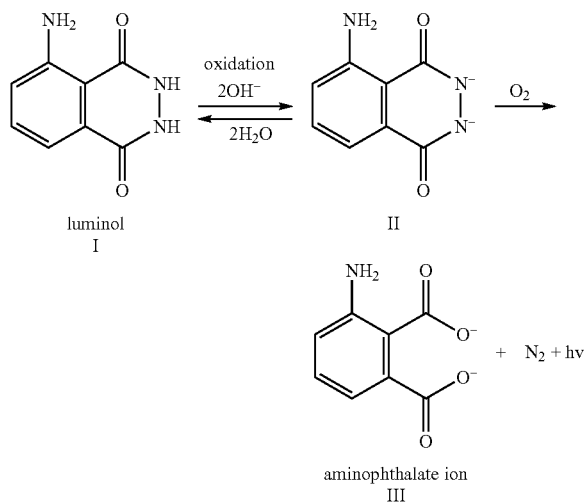

Luminol has long been used as a forensic tool on account of its ability to reveal blood stains. A mixture of luminol, hydrogen peroxide, and a thickening agent can be sprayed on surfaces contaminated with blood traces. If catalyzed by metal ions, such as the iron contained in blood hemoglobin, the mixture will glow.

It has been reported that chemiluminescence-based detection methods can be put into practice with the aid of a microfluidic device—a miniaturized system where liquids flow in channels having cross-sectional dimension of about 0.2 mm. Microfluidic devices are useful analytical tools owing to their ability to reduce reagent consumption, provide well-controlled mixing and particle manipulation, integrate and automate multiple assays (known as lab-on-a-chip), and facilitate imaging and tracking. In the case of chemiluminescence-based detection assays, a microfluidic device will provide improved mixing between the luminol and oxidant, resulting in a higher intensity of emitted light than in a cuvette. The typical glow time when luminol is in contact with an activating oxidant is only approximately 30 sec. However, flow injection allows a continuous glow as long as the molecules and activating oxidants are pumped into the microfluidic device.

For example, a microfluidic device employing a chemiluminescence agent is described in WO 2004/057312, which illustrates the simultaneous analysis of $Cr^{3+}$ and $Cr^{6+}$ by injecting luminol, an oxidant and a mixed sample of $Cr^{3+}$ and $Cr^{6+}$ into a microfluidic device provided with a serpentine-like flow channel.

Kamruzzaman et al. [Biomed Microdevices 15, p. 195-202 (2013)] demonstrated the incorporation of a chemiluminescence system within a microfluidic device. The chemiluminescence system described consists of luminol in an alkaline solution and $AgNO_3$ (a fairly weak oxidant), with added gold nanoparticles (abbreviated AuNPs). The authors report that in the presence of AuNPs, $AgNO_3$ was able to oxidize luminol, generating strong chemiluminescence signal. The luminol-$AgNO_3$—AuNPs system was used for detecting vitamin B12, owing to the ability of cobalt (in the form of its bivalent ion—an important element of vitamin B12) to further enhance the chemiluminescence signal. The average diameter of the AuNPs tested was 11±1 nm.

Experimental work conducted in support of this invention shows that metal nanoparticles-aided chemiluminescence reaction is particle size-dependent. That is, the particle size of the metal nanospheres has an effect on the chemiluminescence intensity of luminol. Results reported below indicate that metal nanoparticles with average size of 10 nm and 20 nm exhibit comparable enhancement, but switching to nanoparticles with larger average particle size, e.g., around 30 nm, leads to stronger enhancement of the chemiluminescence intensity of luminol. It has been also discovered that the intensity of chemiluminescence signal depends on the geometrical features of the microchannel through which the reagents flow, and the position along the channel. Hence microfluidic detectors could be designed to benefit from these findings.

Accordingly, one aspect of the invention relates to the use of noble metal nanoparticles with average particles size of not less than 25 nm, e.g., from 27 nm to 60 nm, as a chemiluminescence enhancer in chemiluminescence-based assays.

Another aspect of the invention is a method for detecting an analyte reactive towards luminol, comprising the steps of: feeding into a reaction chamber an alkaline solution of luminol, noble metal nanoparticles and at least one analyte reactive towards luminol, wherein the reaction chamber is in the form of a curved channel (e.g., having cross-sectional dimension in the range from 0.1 mm to 3 mm, more specifically from 0.15 mm to 0.5 mm);

detecting the light emitted due to a chemiluminescence reaction taking place in said channel; and discharging a reaction mass from said channel, characterized in that the average diameter of the metal nanoparticles is greater than 25 nm (as determined by scanning electron microscope).

Luminol is dissolved in an alkaline aqueous solution and the resultant solution is supplied to the reaction chamber (in basic environment luminol is converted into the corresponding dianion, oxidizable form). Different bases may be used to dissolve luminol in water, such as alkali hydroxide, ammonia and alkali carbonates. The pH of the luminol solution is not less than 8, e.g., from 8 to 10. The concentration of luminol in the solution is preferably not less than 0.01 g/L, e.g., from 0.05 to 0.5 g/L, for example, from 0.1 to 0.2 g/L.

The experimental results reported below show that the system comprising luminol and noble metal nanoparticles as luminescence enhancer is highly sensitive and can detect analytes reactive towards luminol at a very small concentration. Analytes reactive towards luminol include oxidizers, e.g., strong oxidizers such as hypochlorite [e.g., sodium hypochlorite NaOCl or calcium hypochlorite $Ca(OCl)_2$] and halogens. Metal ions such as iron or cobalt ions contained in substances of interest are also reactive toward luminol and can be detected (e.g., in forensic applications for detecting hemoglobin or for detecting vitamin B12 on account of their inclusion of iron and cobalt, respectively). In some embodiments of the invention, an oxidant and an analyte are caused to flow in the reaction chamber, that is, a system comprising luminol-oxidant-noble metal nanospheres is used for detecting an analyte (e.g., metal ion-containing analyte).

As pointed out above, the particle size distribution of the noble (Au, Ag, Pt) metal additive constitutes an important feature of the invention. Metal nanoparticles exhibiting narrow particle size distribution and more preferably near-monodisperse or monodisperse silver or gold nanoparticles with diameter greater than 25 nm, e.g., from 27 nm to 60 nm, emerge from the experimental results reported below as efficient chemiluminescence enhancers. Suitable metal nanoparticles suspensions are commercially available on the market. A stabilizer to prevent particles agglomeration is often present in the commercial suspensions. Protocols for the preparation of suitable nanoparticles can also be found in the literature. For example, preparation of silver nanoparticles with controlled particle size has been described by Zielinska et al. [Procedia Chemistry 1, 1560-1566 (2009)], using sodium borohydride, hydrazine or ascorbic acid to reduce silver ion, optionally in the presence of stabilizers to prevent particles agglomeration. In the case of gold nanoparticles, the precursor is $HauCl_4$; its reduction can be achieved with the aid of sodium borohydride.

The chemiluminescence reaction takes place in a curved channel having cross-sectional dimension from 100 μm to 3000 μm, more specifically from 150 μm to 500 μm, in which the reactants are caused to flow to enable good mixing and readily manageable reaction. By the term "curved channel" is meant that the flow channel comprises at least one curve (curved section), as described in more detail below. The channel is part of a microfluidic device, which can be fabricated in poly(dimethylsiloxane), e.g., by casting this elastomeric transparent polymer (abbreviated PDMS) against models that are usually created with the aid photolithography, as described for example by McDonald et al. in Electrophoresis 21, p. 27-40 (2000). Suitable fabrication methods can also be found in WO 2004/057312 and Kamruzzaman et al. (supra).

One convenient approach to fabricating a microfluidic device suitable for use in the present invention begins by creating a layout for the device in a computer-aided-design program. Then a 'master' is produced (a photo-curable epoxy, e.g., SU-8 features deposited on a silicon wafer). Next, the PDMS pre-polymer (commercially available as two-part resin system which on mixing produces the polymer) is poured onto the master. The PDMS replica is cured, generating a negative replica of the master (ridges of the master appear as valleys in the replica). The replica is peeled from the master and assembled into the final device. That is, access holes are added to the cured layer to enable the feeding and discharge of fluids, i.e., inlet(s) and outlet openings are made at the appropriate positions. Now the replica is sealed to provide the "missing" fourth wall of the channel by bonding to another surface (PDMS or glass). Sealing is achieved by exposure of the PDMS replica and the other surface to a treatment in a plasma chamber and then contacting same to accomplish the bonding. The pre-prepared inlet openings are connected with tubes to suitable reservoirs where the reagents are kept whereas the outlet opening is connected to a vessel to enable collection of the continuously discharged reaction mass.

The microfludic device is equipped with suitable pumps (e.g., syringe pumps, peristaltic pumps, plunger pumps) to move the liquids along the channel, typically at flow rates in the range from 0.1 μL/sec to 0.5 μL/sec preferably from 0.25 to 0.45 μL/sec.

A detector is typically placed outside the microfludic device to measure the intensity of the light emitted by the chemiluminescence reaction. The detector may include a charge-coupled-device (CCD), pothomultiplier tube (PMT) or photodiode. If the concentration of an analyte in a sample should be determined by the method of the invention, then this will be achieved with the aid of pre-prepared intensity versus concentration curves, which will be used by the detector and suitable software to quantify the analyte in the sample.

As pointed out above, the flow channel comprises at least one curved section. This geometrical motif may be incorporated into the channel in different ways. For example, in FIG. 2c two straight, essentially parallel, sections of the flow channel are shown to be connected by a curved section (e.g., a toroidal section of small radius) which joins the straight sections smoothly. The length L of each of the individual straight sections may range from 400 μm to 1000 μm. The straight sections are separated about 1-5 mm apart. The radius R of the curved section is defined as the distance of the (inner) wall of the bend from the center of the imaginary line drawn between the edges of the parallel straight sections (just before they start to bent); preferably, that is, 50 μm≤R≤200 μm.

A channel incorporating the geometrical motif illustrated in FIG. 2c may have a serpentine-like shape, as shown in FIG. 1 that is discussed in more detail in the experimental section below. But other curved shapes, e.g., spiral-shaped channels as illustrated by Kamruzzaman et al. are also useful.

Based on the finding reported in the experimental results below, that the strongest enhancement generated by the noble metal nanoparticles occurs immediately after the first curve in the flow channel, the invention also provides a miniaturized microfluidic device adapted for luminescence-based detection, comprising:

A) a curved channel fabricated in a suitable material, e.g., in poly(dimethylsiloxane), having cross-sectional dimension from 0.1 mm to 3 mm, more specifically from 0.15 mm to 0.5 mm; wherein the flow channel consists of a pair of straight, essentially parallel sections connected by a curved section joining the straight sections smoothly, wherein the length L of each of the individual straight sections is from 400 μm to 1000 μm and the radius R of the curved section is from 50 μm to 200 μm, B) a set of reservoirs and pumps for holding and delivering into said flow channel:
solution of a luminescence reagent (e.g., an alkaline solution of luminol), luminescence enhancer comprising noble metal nanoparticles (preferably with average particle size of not less than 25 nm);

sample comprising an analyte reactive towards luminol; wherein said reservoirs are connected through tubes to input opening(s) of the flow channel, C) a detector for measuring the intensity of the light emitted by the luminescence reaction; and optionally D) a vessel to which the reaction mixture is withdrawn.

EXAMPLES

Example 1 (Reference), 2-5 (Comparative) and 6-7 (of the Invention)

The microluidic device used in the experiment comprises a serpentine-like channel formed in PDMS by the technique described above. We have designed and fabricated a reusable microflow device with a serpentine channel 200 µm in width, 200 µm in depth and 600 µm in length (for a single straight chain). The PDMS channel was molded over the 3D printed device. The layout for the mold was designed using the CAD Autodesk inventor (Stockport, UK). After printing, the channels were sealed using oxygen plasma for 30 s.

Figure 1A:
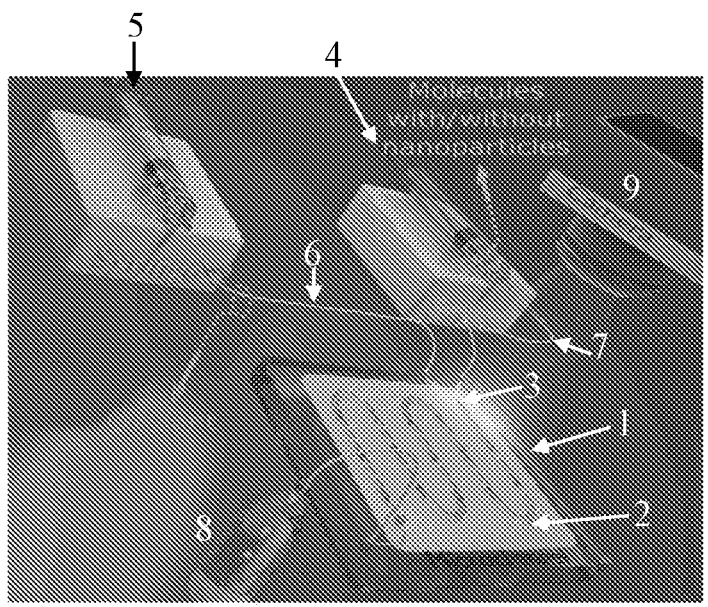
FIG. 1a is a photograph of a microfluidic device comprising a serpentine-like channel, syringes for feeding reagents and a charge-coupled-device detecting emitted light.
Figure 1B:
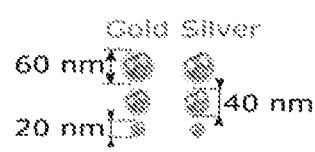
FIGS. 1b and 1c illustrate noble metal nanoparticles (1b) that were added to the serpentine-like channel (1c).
Figure 1C:
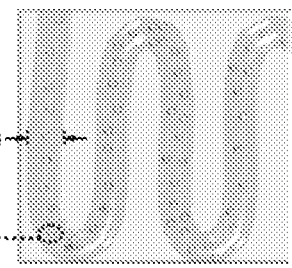

An illustrative microfluidic device is shown in FIG. 1. In the one used in the experiment, the so-formed channel (1) consisted of eight straight parallel sections. Each pair of adjacent sections is connected by a toroidal section (2) of small radius which joins the straight sections smoothly, thereby creating a flow path with a serpentine-like shape. The straight sections are designated herein by Roman numbers I to VIII. The opening (3) of section I functions as a port for feeding the reagents. A first syringe (4) is used to inject an alkaline solution comprising luminol and the tested additive. A second syringe (5) is used to inject an aqueous solution of the agent reactive towards luminol. The diameter of the syringes is 180 µm. The outlet openings of the two syringes are connected to the opening (3) via 0.2 mm tubes (6) and (7), respectively. The reaction products are discharged through the open end of the last straight section and are collected in to vessel (8). The intensity of emitted light was detected (9) by a charge-coupled-device (CCD), Lumenera Infinity 2-3C (from Lumenera Corporation, Canada).

The additives tested are gold and silver nanoparticles, available commercially from BBI or Sigma Aldrich in the form of suspensions in water stabilized with polyethylene glycol. Suspensions of monodisperse metal nanoparticles are available in various sizes. The properties of the additives tested are set out in Table 1 (information according to manufacturer):

TABLE 1

|  | Particles radius (nm) | Concentration (number per ml) |
|---|---|---|
| Gold nanoparticles | 10 | $7 \times 10^{11}$ |
|  | 20 | $9 \times 10^{10}$ |
|  | 30 | $2.6 \times 10^{10}$ |
| Silver nanoparticles | 10 | $7 \times 10^{10}$ |
|  | 20 | $9 \times 10^{9}$ |
|  | 30 | $2.6 \times 10^{9}$ |

The Solutions used in the experiments are tabulated below:

TABLE 2

| Ex. | Reagent in syringe 1 | Solution in syringe 2 |
|---|---|---|
| Reference Example | | |
| 1 | 0.4 g luminol dissolved in an alkaline solution (4 g NaOH dissolved in 1950 ml water) | 50 mg of NaOCl dissolved in 1950 ml water |
| Comparative Examples | | |
| 2 | 0.2 g luminol dissolved in an alkaline solution (2 g NaOH dissolved in 1950 ml water) Additive: 50 ml gold nanoparticles suspension (r = 10 nm) | 50 mg of NaOCl dissolved in 1950 ml water |
| 3 | 0.2 g luminol dissolved in an alkaline solution (2 g NaOH dissolved in 1950 ml water) Additive: 50 ml gold nanoparticles suspension (r = 20 nm) | 50 mg of NaOCl dissolved in 1950 ml water |
| 4 | 0.2 g luminol dissolved in an alkaline solution (2 g NaOH dissolved in 1950 ml water) Additive: 50 ml silver nanoparticles suspension (r = 10 nm) | 50 mg of NaOCl dissolved in 1950 ml water |
| 5 | 0.2 g luminol dissolved in an alkaline solution (2 g NaOH dissolved in 1950 ml water) Additive: 50 ml silver nanoparticles suspension (r = 20 nm) | 50 mg of NaOCl dissolved in 1950 ml water |
| Examples of the Invention | | |
| 6 | 0.2 g luminol dissolved in an alkaline solution (2 g NaOH dissolved dissolved in ml water) Additive: 50 ml gold nanoparticles suspension (r = 30 nm) | 50 mg of NaOCl dissolved in 1950 ml water |
| 7 | 0.2 g luminol dissolved in an alkaline solution (2 g NaOH dissolved in ml water) Additive: 50 ml silver nanoparticles suspension (r = 30 nm) | 50 mg of NaOCl dissolved in 1950 ml water |

Several experiments were conducted at different flow rates of the reagents, in the range from 0.1 µL/sec to 0.5 µL/sec. The results reported below correspond to the experiments where the flow rate was 0.35 µL/sec, seeing that the maximal chemiluminescence intensity was obtained at said flow rate.

The limit of detection for the experimental setup was determined using 3 standard deviations and 20 repeats of images for each individual point, and was estimated to be less than 110 µg/mL.

Figure 2A:
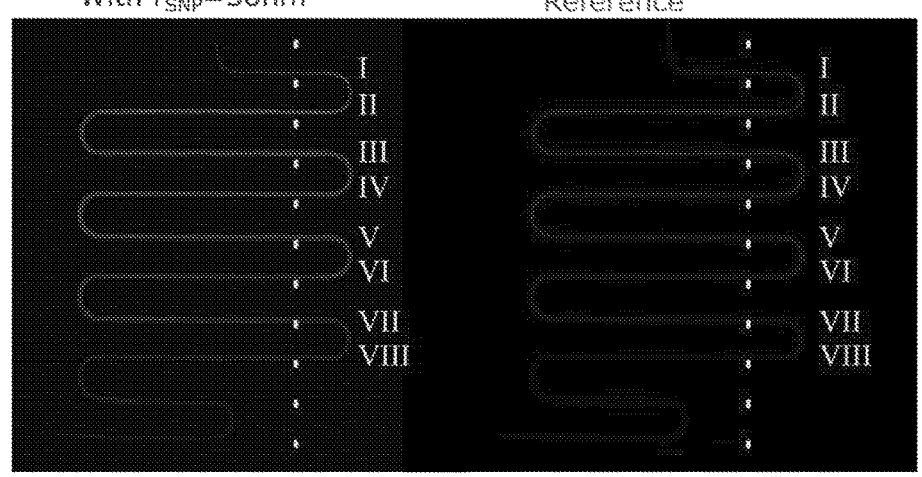
FIG. 2a shows the reaction chamber of Example 6 (with gold nanoparticles) on the left side, and the reaction chamber of Reference Example 1 (without additives) on the right side.
Figure 2B:
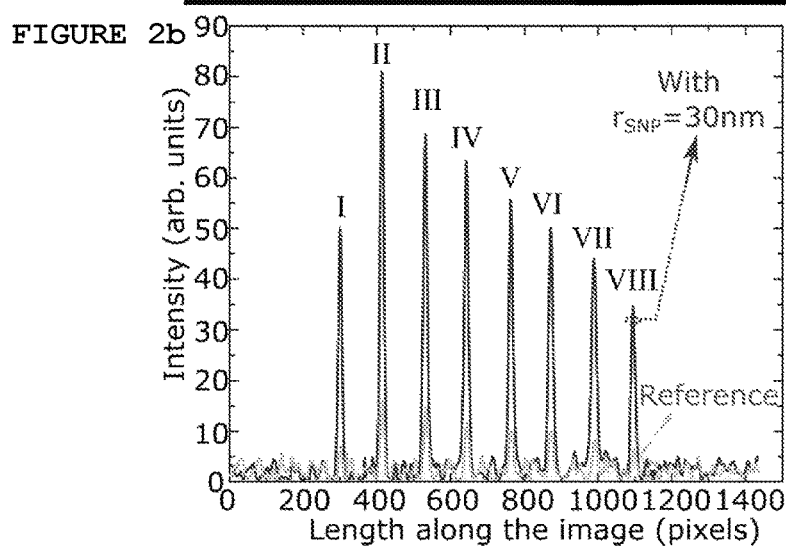
FIG. 2b is a plot of the luminescence intensity versus position along the flow path (serpentine arm).
Figure 2C:
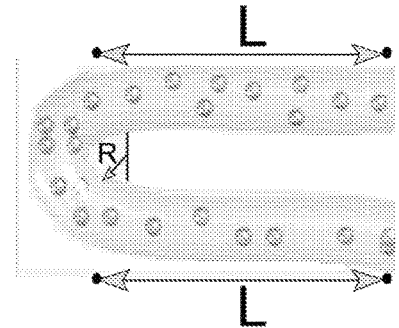
FIG. 2c is an illustration of a part of the serpentine-like channel, consisting of two straight, essentially parallel sections joined by a curved section.

In general, the experimental results captured by the CCD camera show a glowing serpentine channel for Examples 2 to 7, as opposed to a barely seen serpentine channel in the case of Reference Example 1 (devoid of any additive). Illustrative images corresponding to Example 6 (gold nanoparticles with radii of 30 nm used as chemiluminescence enhancer) vis-à-vis Reference Example 1 are provided in FIG. 2a—left and right images, respectively.

Figure 3A:
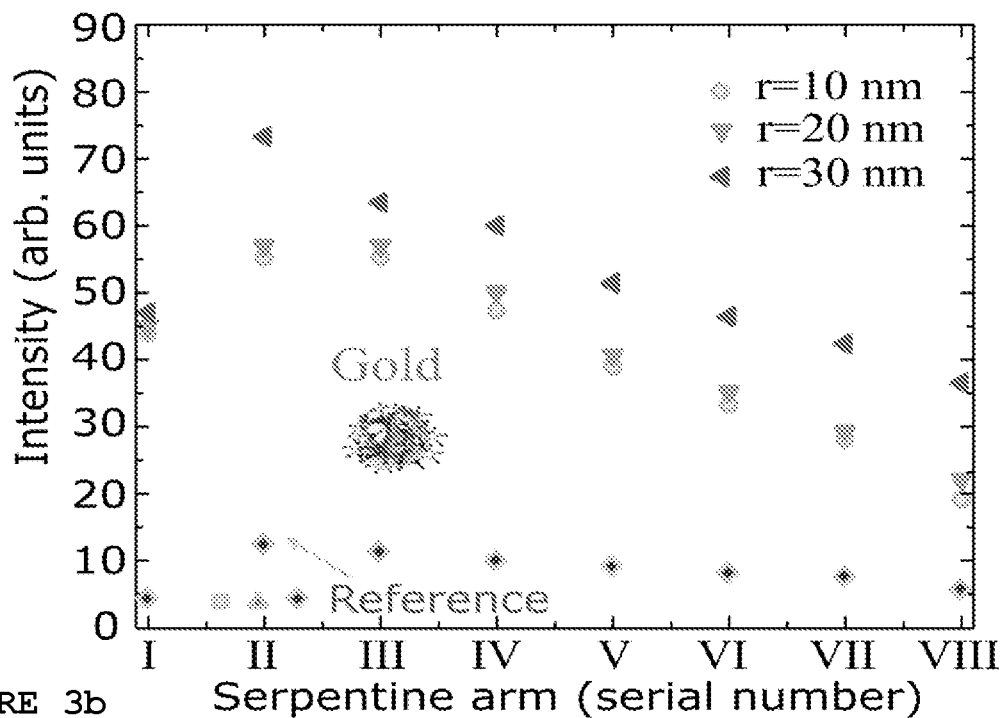
FIGS. 3a and 3b are plots of luminescence intensity versus serpentine arm for gold (3a) and silver (3b) nanoparticles.
Figure 3B:
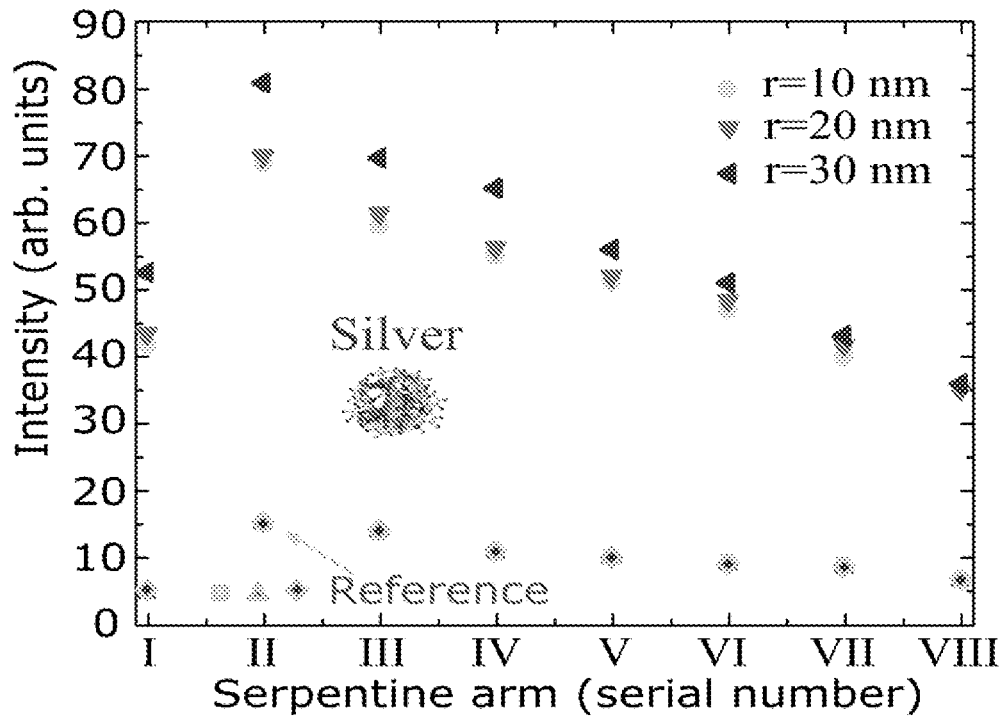

Aside from images taken by a CCD camera, the results can also be presented graphically by plotting the intensity of the chemiluminescence emission of luminol as a function of the position along the flow path. That is, the intensity is measured for each of the straight sections of the serpentine-like channel—serpentine arms I-VIII. The results are presented in FIGS. 3a and 3b, for the additives consisting of gold nanoparticles and silver nanoparticles, respectively: FIG. 3a corresponds to Examples 2, 3 and 6 and FIG. 3b corresponds to Examples 4, 5 and 7. The results for the Reference Example 1 are included in both graphs, and are indicated by rhombuses. The following observations can be made:

(i) The results indicate that the addition of either gold nanoparticles or silver nanoparticles produces strong enhancement of the chemiluminescence intensity of luminol. For both metals, nanospheres with average size of 10 nm and 20 nm produce essentially the same effect. But further increase of the particle size of the metal additive to 30 nm leads to a noticeable increase in the enhancement of the chemiluminescence intensity of luminol.

(ii) Taking into consideration the different concentrations of silver and gold in the commercially available suspensions used (see Table 1), one may conclude that silver nanoparticles induce a stronger enhancement of chemiluminescence than gold nanoparticles. The enhancement of luminol emission using silver nanospheres is stronger by a factor of up to 90 compared to using the same concentration of gold nanospheres.

(iii) The results also illustrate the change in the intensity of emission with the distance along the serpentine channel, seeing that the strongest enhancement occurs in arm II, which can be understood to indicate the best mixing between reagents in this arm and/or the most favorable distance between the light emitting species and "nanoantennas". The mixing in the microfluidic device occurs based on the diffusion of particles from one laminar layer into the adjacent one. Efficient mixing occurs around the bends due to the Dean flow; therefore, arm II after the first bend shows the highest chemiluminescence intensity.

What is claimed is:

1. A method for detecting an analyte reactive towards luminol, comprising:
   feeding into a reaction chamber an alkaline solution of luminol, noble metal nanoparticles and at least one analyte reactive towards luminol, wherein the reaction chamber is in the form of a curved channel having serpentine-like shape, such that the form of the reaction chamber curves in alternate directions;
   detecting a light emitted due to a chemiluminescence reaction taking place in said curved channel; and
   discharging a reaction mass from said curved channel,
   wherein the average diameter of the noble metal nanoparticles is greater than 25 nm, wherein the curved channel comprises a plurality of straight sections including at least a first straight section, a second straight section, and a third straight section, which are parallel with each other, and wherein the straight sections are connected by a curved section, which joins the straight sections smoothly, creating the serpentine-like shape, and wherein a length L of each of the straight sections is from 400 µm to 1000 µm and a radius R of the curved section is from 50 µm to 200 µm, and wherein an enhancement of the light emitted by the chemiluminescence reaction in the second straight section is greater than an enhancement of the light emitted by the chemiluminescence reaction in the first and third straight sections.

2. A method according to claim 1, wherein the noble metal nanoparticles are selected from the group consisting of gold and silver.

3. A method according to claim 2, wherein the noble metal nanoparticles are silver.

4. A method according to claim 1, wherein the curved channel has cross-sectional dimension in the range from 0.15 mm to 0.5 mm.

5. A method according to claim 1, wherein reagents and reactants are fed into the reaction chamber at flow rates from 0.1 µL/sec to 0.5 µL/sec.

6. A method according to claim 5, wherein the flow rate is from 0.25 to 0.45 µL/sec.

7. A method for detecting an analyte reactive towards luminol, comprising:
   feeding into a reaction chamber an alkaline solution of luminol, noble metal nanoparticles and at least one analyte reactive towards luminol, wherein the reaction chamber is in the form of a curved channel having serpentine-like shape, wherein the curved channel is not spiral-shaped;
   detecting a light emitted due to a chemiluminescence reaction taking place in said curved channel; and
   discharging a reaction mass from said curved channel,
   wherein the curved channel consists of a plurality of straight sections including a first straight section, a second straight section, and a third straight section, which are parallel with each other, connected by a curved section, which joins the straight sections smoothly, creating the serpentine-like shape, and wherein a length L of each of the straight sections is from 400 µm to 1000 µm and a radius R of the curved section is from 50 µm to 200 µm, and wherein an enhancement of the light emitted by the chemiluminescence reaction in the second straight section is greater than an enhancement of the light emitted by the chemiluminescence reaction in the first and third straight sections.

8. A microfluidic device adapted for luminescence-based detection, comprising:
   A) a curved channel which has serpentine-like shape, having cross-sectional dimension from 0.15 mm to 0.5 mm; wherein the curved channel is not spiral-shaped, and wherein the flow channel consists of a plurality of straight sections including a first straight section, a second straight section, and a third straight section, essentially parallel sections connected by a curved section joining the straight sections smoothly, creating the serpentine-like shape, and wherein the length L of each of the individual straight sections is from 400 µm to 1000 µm and the radius R of the curved section is from 50 µm to 200 µm, and wherein an enhancement of the light emitted by the chemiluminescence reaction in the second straight section is greater than an enhancement of the light emitted by the chemiluminescence reaction in the first and third straight sections;
   B) a plurality of reservoirs and pumps for holding and delivering into said flow channel:
   a solution of a luminescence reagent,
   a luminescence enhancer comprising noble metal nanoparticles;
   a sample comprising an analyte reactive towards luminol;
   wherein said reservoirs are connected through tubes to input opening(s) of the flow channel, C) a detector for measuring the intensity of the light emitted by the luminescence reaction; and optionally D) a vessel to which the reaction mixture is withdrawn.

9. A microfluidic device according to claim 8, wherein the curved channel is fabricated in poly(dimethylsiloxane).

\* \* \* \* \*